United States Patent
Wilke et al.

(10) Patent No.: US 11,684,353 B2
(45) Date of Patent: Jun. 27, 2023

(54) TISSUE-FRIENDLY ENHANCED FRICTION SURFACE FOR SURGICAL RETRACTORS

(71) Applicant: UNIVERSITY OF FLORIDA RESEARCH FOUNDATION, INCORPORATED, Gainesville, FL (US)

(72) Inventors: Benjamin K. Wilke, Ponte Vedra Beach, FL (US); Bradley S. Schoch, Ponte Vedra Beach, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 298 days.

(21) Appl. No.: 16/644,542

(22) PCT Filed: Sep. 11, 2018

(86) PCT No.: PCT/US2018/050364
§ 371 (c)(1),
(2) Date: Mar. 5, 2020

(87) PCT Pub. No.: WO2019/051454
PCT Pub. Date: Mar. 14, 2019

(65) Prior Publication Data
US 2020/0383671 A1 Dec. 10, 2020

Related U.S. Application Data

(60) Provisional application No. 62/591,382, filed on Nov. 28, 2017, provisional application No. 62/556,548, filed on Sep. 11, 2017.

(51) Int. Cl.
*A61B 17/02* (2006.01)
*B33Y 10/00* (2015.01)
(Continued)

(52) U.S. Cl.
CPC .............. *A61B 17/02* (2013.01); *B33Y 10/00* (2014.12); *B33Y 50/02* (2014.12); *B33Y 80/00* (2014.12);
(Continued)

(58) Field of Classification Search
CPC .......... A61B 17/02; A61B 2017/00858; A61B 2017/0237; A61B 2017/0243
See application file for complete search history.

(56) References Cited

U.S. PATENT DOCUMENTS

| 4,048,987 A | 9/1977 | Hurson |
| 5,860,987 A | 1/1999 | Ratcliff et al. |

(Continued)

FOREIGN PATENT DOCUMENTS

| KR | 2009-0075531 A | 7/2009 | |
| WO | WO-2017/062424 A1 | 4/2017 | |
| WO | WO-2018021174 A1 * | 2/2018 | ....... A61B 17/00234 |

OTHER PUBLICATIONS

Shibata, Toshihiko, et al. WO2018/021174 Machine Translation, retrieved Feb. 3, 2023 (Year: 2023).*

(Continued)

*Primary Examiner* — Kevin T Truong
*Assistant Examiner* — Tracy L Kamikawa
(74) *Attorney, Agent, or Firm* — Alston & Bird LLP (57) ABSTRACT

A tissue contact surface for use on a surgical retractor is provided. The tissue contact surface comprises a generally smooth surface; and a plurality of partial ellipsoid surfaces extending out and away from the generally smooth surface. The plurality of partial ellipsoid surfaces comprise a first partial ellipsoid surface and an adjacent second partial ellipsoid surface. The first partial ellipsoid surface extends approximately 0.5 millimeters to 1 centimeter out from the generally smooth surface. A spacing between the first partial (Continued)

ellipsoid surface and the second partial ellipsoid surface is approximately 0.5 millimeters to 1 centimeter. In various embodiments, the plurality of partial ellipsoid surfaces are 3D printed onto the generally smooth surface.

8 Claims, 5 Drawing Sheets

(51) Int. Cl.
    *B33Y 50/02*     (2015.01)
    *B33Y 80/00*     (2015.01)
    *A61B 17/00*     (2006.01)

(52) U.S. Cl.
    CPC ............... *A61B 2017/00526* (2013.01); *A61B 2017/00858* (2013.01)

(56) References Cited

U.S. PATENT DOCUMENTS

| | | | |
|---|---|---|---|
| 6,478,029 B1 | 11/2002 | Boyd et al. | |
| 6,685,632 B1 | 2/2004 | Hu et al. | |
| 6,837,851 B1 | 1/2005 | Valentini et al. | |
| 6,994,669 B1 | 2/2006 | Gannoe et al. | |
| 7,922,657 B2 | 4/2011 | Gillinov et al. | |
| 8,273,102 B2 | 9/2012 | Danitz et al. | |
| 8,679,005 B2 | 3/2014 | Gutierrez et al. | |
| 9,492,154 B2 | 11/2016 | Melsheimer et al. | |
| 2010/0280325 A1* | 11/2010 | Ibrahim ................ | A61B 17/02 600/206 |
| 2014/0024900 A1 | 1/2014 | Capote et al. | |
| 2014/0066719 A1 | 3/2014 | Nichter | |
| 2014/0323811 A1* | 10/2014 | DeSantis ................ | A61B 17/02 600/245 |
| 2016/0015497 A1 | 1/2016 | Vayser et al. | |
| 2016/0151058 A1* | 6/2016 | Ferro .................... | A61B 17/02 600/215 |
| 2017/0071587 A1 | 3/2017 | Harshman et al. | |
| 2017/0095242 A1 | 4/2017 | Milbocker et al. | |

OTHER PUBLICATIONS

Hunsaker, Darrell H. *A New Set Of Parotidectomy Retractors*, Otolaryngology—Head and Neck Surgery, Sep. 1990, vol. 103, No. 3, pp. 497-499. DOI: 10.1177/019459989010300328.

* cited by examiner

| Surface | Translational Force (grams) | | | | |
|---|---|---|---|---|---|
| | Test 1 | Test 2 | Test 3 | Test 4 | Average |
| Control Surface - No partial ellipsoid surfaces | 75 | 175 | 150 | 200 | 150 |
| First Test Surface - 1 mm diameter partial spheroids | 200 | 150 | 150 | 225 | 181.25 |
| Second Test Surface - 2 mm diameter (short) | 250 | 125 | 175 | 175 | 181.25 |
| Third Test Surface - 2mm diameter (long) | 200 | 200 | 200 | 175 | 193.75 |
| Fourth Test Surface - Variable (3 mm and 1 mm diameter) | 325 | 175 | 200 | 125 | 206.25 |
| Fifth Test Surface - Variable (3 mm and 2 mm diameter) | 250 | 175 | 175 | 175 | 193.75 |

TISSUE-FRIENDLY ENHANCED FRICTION SURFACE FOR SURGICAL RETRACTORS

CROSS REFERENCE TO RELATED APPLICATIONS

This application is a National Stage Application, filed under 35 U.S.C. § 371, of International Application No. PCT/US2018/050364, filed Sep. 11, 2018, which claims priority to U.S. Provisional Application No. 62/591,382, filed Nov. 28, 2017, and U.S. Provisional Application No. 62/556,548, filed Sep. 11, 2017; the content of both of which are hereby incorporated in their entirety.

BACKGROUND

Related Field

Embodiments of the present invention relate generally to surgical retractors. For example, an example embodiment, provides a tissue-friendly enhanced friction surgical retractor surface. An example embodiment provides a surgical retractor having a tissue-friendly enhanced friction surgical retractor surface.

Description of Related Art

Conventional surgical retractors come in a variety of shapes and sizes. Some have a smooth surface in order to retract without damage to the underlying tissue, whereas other retractors have sharp ends in order to grab into the tissue for their holding power. While the sharper retractors have a tendency to provide improved retraction with a lower chance of slipping, these are not able to be used around certain delicate or cancerous tissue due to the concern for damage to the tissue or contamination of the cancer. The inability to use sharp retractors in certain situations has left a need for a retractor with a surface that will provide increased friction (and therefor stability) while also being gentle to the surrounding tissues.

BRIEF SUMMARY

Example embodiments provide a surface texture for surgical retractors that is composed of a plurality of partial ellipsoid surface. This surface texture may be placed on any retractor in order to increase the friction between the retractor and the tissue without damaging the tissue or underlying structures. Example embodiments provide a surgical retractor having a surface texture that increases the friction between the retractor and the tissue without damaging the tissue or underlying structures.

In an example embodiment, a tissue contact surface for use on a surgical retractor is provided. In an example embodiment, the tissue contact surface comprises a generally smooth surface; and a plurality of partial ellipsoid surfaces extending out and away from the generally smooth surface. The plurality of partial ellipsoid surfaces comprise a first partial ellipsoid surface and an adjacent second partial ellipsoid surface. The first partial ellipsoid surface extends approximately 0.5 millimeters to 1 centimeter (e.g., 0.75-1.25 millimeters) out from the generally smooth surface. A spacing between the first partial ellipsoid surface and the second partial ellipsoid surface is approximately 0.5 millimeters to 1 centimeter (e.g., 0.75-1.25 millimeters).

In an example embodiment, a surgical retractor is provided. In an example embodiment, the surgical retractor comprises a blade having a tissue contact surface. The tissue contact surface comprises a generally smooth surface of the blade; and a plurality of partial ellipsoid surfaces extending out and away from the generally smooth surface. The plurality of partial ellipsoid surfaces comprise a first partial ellipsoid surface and an adjacent second partial ellipsoid surface. The first partial ellipsoid surface extends approximately 0.5 millimeters to 1 centimeter (e.g., 0.75-1.25 millimeters) out from the generally smooth surface. A spacing between the first partial ellipsoid surface and the second partial ellipsoid surface is approximately 0.5 millimeters to 1 centimeter (e.g., 0.75-1.25 millimeters).

In an example embodiment, a method for producing a surgical retractor is provided. In an example embodiment, the method comprises controlling a 3D printer, via a computing entity, to cause the 3D printer to print a defined array of partial ellipsoid surfaces. The defined array of partial ellipsoid surfaces comprises a plurality of partial ellipsoid surfaces. The defined array of partial ellipsoid surfaces are printed onto a generally smooth surface. Each of the plurality of partial ellipsoid surfaces extends out and away from the generally smooth surface. The plurality of partial ellipsoid surfaces comprise a first partial ellipsoid surface and an adjacent second partial ellipsoid surface. The first partial ellipsoid surface extends approximately 0.5 millimeters to 1 centimeter (e.g., 0.75-1.25 millimeters) out from the generally smooth surface. A spacing between the first partial ellipsoid surface and the second partial ellipsoid surface is approximately 0.5 millimeters to 1 centimeter (e.g., 0.75-1.25 millimeters).

In an example embodiment, the generally smooth surface is a blade of the retractor. In an example embodiment, the generally smooth surface is a portion of a handle of the retractor.

In an example embodiment, the generally smooth surface is a substrate configured to be secured to at least one of a blade of the retractor or a portion of a handle of the retractor and the method further comprises securing the substrate to one of the blade or the portion of the handle.

BRIEF DESCRIPTION OF THE FIGURES

Having thus described the invention in general terms, reference will now be made to the accompanying drawings, which are not necessarily drawn to scale, and wherein:

DETAILED DESCRIPTION OF VARIOUS EMBODIMENTS

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. The term "or" (also denoted "/") is used herein in both the alternative and conjunctive sense, unless otherwise indicated. The terms "illustrative" and "exemplary" are used to be examples with no indication of quality level. The terms "generally" and "approximately" refer to within engineering and/or manufacturing limits or allowances, unless otherwise indicated. Like numbers refer to like elements throughout.

Figure 1:
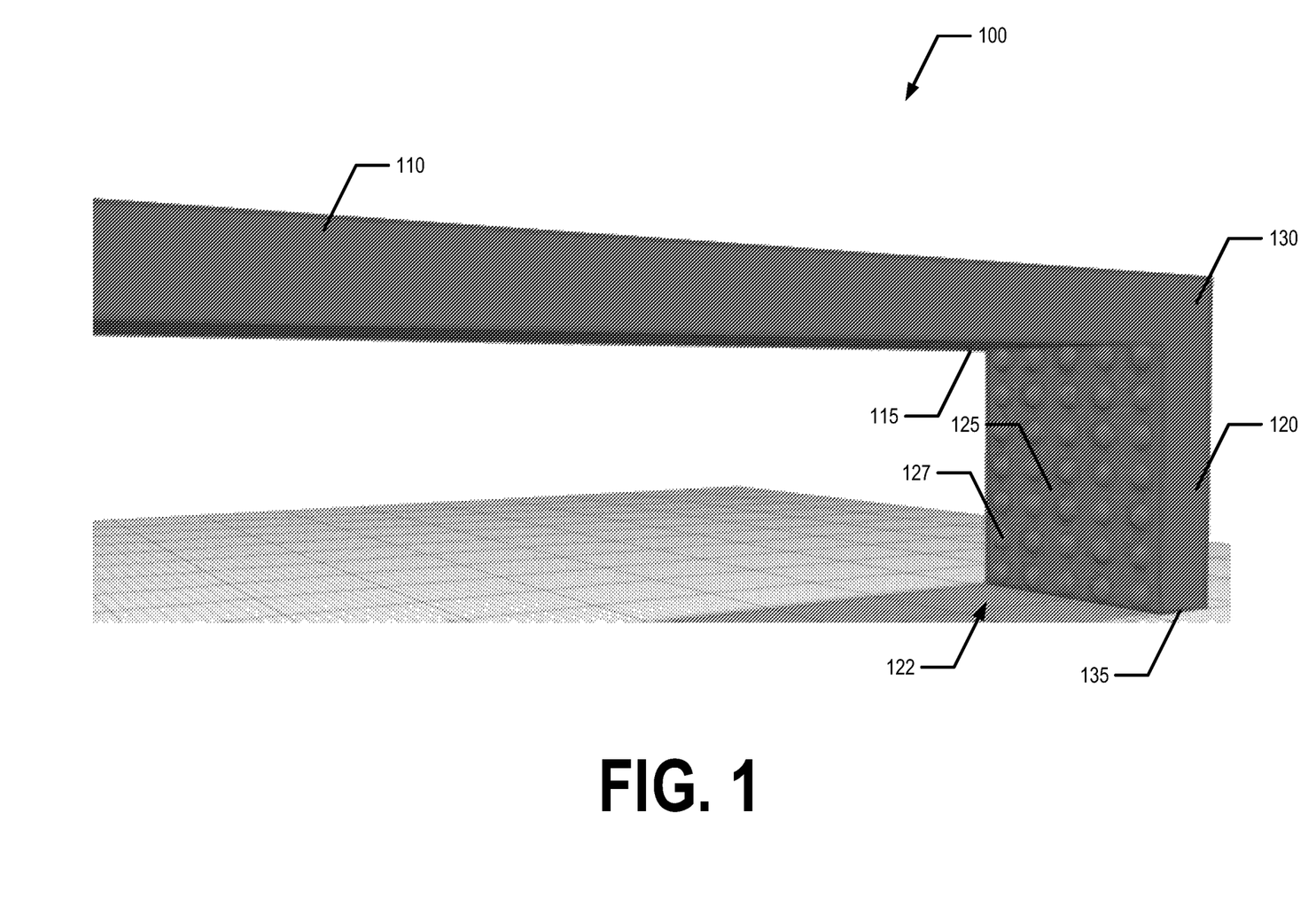
FIG. 1 provides a schematic diagram of a surgical retractor in accordance with an example embodiment.

As shown in FIG. 1, a surgical retractor 100 comprises a handle 110 and a blade 120. The handle 110 may be configured to be held by a surgeon, nurse, and/or the like during a surgical procedure. The blade 120 is configured and/or operable to retract and/or expose tissue during a surgical procedure. In an example embodiment, the blade 120 is fixedly secured to the handle 110 at angle 130. The blade 120 extends from the angel 130 to a free end 135. A surface of the blade 120 comprises a tissue contact surface 122. For example, in an example embodiment, the tissue contact surface 122 is disposed on a surface of the blade 120 extending from the angle 130 to the free end 135 that is at an acute, right, or obtuse angle to a first surface 115 of the handle 110. For example, the angle between the tissue contact surface and the first surface 115 of the handle 110 is less than 180 degrees. The tissue contact surface 122 is configured and/or operable to provide increased friction between the tissue and the tissue contact surface 122 (e.g., compared to a surgical retractor having only a generally smooth planar surface) without damaging and/or while minimizing damage to the tissue contacted by the tissue contact surface 122. In an example embodiment, some or all of the edges of the surgical retractor 100 and/or of the blade 120 are generally smooth, curved, bull-nosed, rounded, and/or not sharp.

In an example embodiment, the tissue contact surface 122 comprises a generally smooth surface 125 and a plurality of partial ellipsoid surfaces 127. For example, the plurality of partial ellipsoid surfaces 127 form a partial ellipsoid array on the generally smooth surface 125. In an example embodiment, the generally smooth surface 125 is a generally smooth planar surface. In an example embodiment, the generally smooth surface 125 may be a generally smooth curved surface (e.g., concave, convex, having a combination of planar, convex, and/or concave portions, and/or the like).

In an example embodiment, each of the partial ellipsoid surfaces 127 may be a portion of the surface of a hollow ellipsoid (e.g., the partial ellipsoid may be hollow). In another example embodiment, each of the partial ellipsoid surfaces 127 may be a portion of the surface of a solid ellipsoid. In an example embodiment, each partial ellipsoid surface 127 defines a major axis, an intermediate axis, and a minor axis. In an example embodiment, each of the major axis, intermediate axis, and minor axis of a partial ellipsoid surface 127 is within the range of 0.5 millimeters to 1 centimeter. In an example embodiment, the major axis, intermediate axis, and minor axis are approximately equal. For example, in an example embodiment, at least one of the partial ellipsoid surfaces 127 is a partial spherical surface. In an example embodiment, all of the partial ellipsoid surfaces 127 are partial spherical surfaces. For example, in one embodiment, all of the partial ellipsoid surfaces 127 are partial spherical surfaces (e.g., hemispheres) defined by a radius of 1 millimeter. In an example embodiment, at least one of the partial ellipsoid surfaces 127 is a portion of an ellipsoid of revolution. For example, the partial ellipsoid surface 127 may have two axes (e.g., the major axis and the intermediate axis or the intermediate axis and the minor axis) that are the same length. In another example embodiment, each of the axes of at least one of the partial ellipsoid surfaces 127 are different lengths.

In an example embodiment, the partial ellipsoid surfaces 127 extend outward and away from the generally smooth surface 125. In an example embodiment, an axis of a partially ellipsoid surface 127 is parallel to the normal of the generally smooth surface 125 at the location of the partial ellipsoid surface on the generally smooth surface. For example, an axis of the partial ellipsoid surface 127 may be perpendicular to the generally smooth surface at the location of the partial ellipsoid surface 127. In an example embodiment, an axis of at least one partial ellipsoid surface 127 is at an angle that is less than 90 degrees from the normal of the generally smooth surface 125 at the location of the partial ellipsoid surface. For example, the partial ellipsoid surface 127 may be partially inclined with respect to the normal of the generally smooth surface at the location of the partial ellipsoid surface. For example, in an example embodiment, at least one of the partial ellipsoid surfaces 127 may extend out and away from the generally smooth surface 125 at an angle that is not perpendicular to the generally smooth surface. In an example embodiment, the location of the partial ellipsoid surface is the center point of the ellipse (or circle or polygon) formed by the intersection of the partial ellipsoid surface with the generally smooth surface.

In an example embodiment, each of the partial ellipsoid surfaces 127 that form the partial ellipsoid array on the surgical retractor 100 are the same size. In an example embodiment, the partial ellipsoid surfaces 127 that form the partial ellipsoid array on the surgical retractor vary in size and/or shape. For example, some of the partial ellipsoid surfaces 127 may have their major axis aligned with a first axis 140 (see FIG. 2B) of the blade 120 and some of the partial ellipsoid surfaces 127 may have their minor axis aligned with the first axis 140. In another example, some of the partial ellipsoid surfaces 127 of the partial ellipsoid array may define major, intermediate, and minor axes of a first set of lengths (e.g., a, b, and c) and other partial ellipsoid surfaces 127 of the partial ellipsoid array may define major, intermediate, and minor axes of a second set of lengths (e.g., A, B, and C), wherein the first set of lengths and the second set of lengths vary in at least one corresponding element (e.g., at least one of (a) a is not equal to A, (b) b is not equal to B, or (c) c is not equal to C).

In an example embodiment, the partial ellipsoid surfaces 127 form a partial ellipsoid array that is only on the generally smooth surface 125 of the blade 120. In one example embodiment, the partial ellipsoid surfaces 127 may form a partial ellipsoid array that is disposed on the generally smooth surface 125 of the blade 120 and at least a portion of the first surface 115 of the handle 110. Thus, in an example embodiment, a surgical retractor may comprise a first tissue contact surface formed and/or disposed on the blade 120 and a second tissue contact surface formed and/or disposed on the first surface 115 of the handle 110. The first and second tissue contact surfaces may be transverse to one another. For example, a plane defined by the first generally smooth surface 125 of the blade 120 and a plane defined by a second generally smooth surface of the first surface of the handle 115 may be transverse and/or perpendicular to one another.

In an example embodiment, the partial ellipsoid surfaces 127 are formed and/or molded directly onto the generally smooth surface 125. For example, the partial ellipsoid surfaces are 3D printed onto the generally smooth surface 125, in an example embodiment. In an example embodiment, the partial ellipsoid surfaces 127 are formed and/or molded onto an intermediate generally smooth surface that is configured to be secured and/or fixed onto a generally smooth surface 125 of the retractor. For example, the partial ellipsoid surfaces are 3D printed onto a generally smooth surface of a substrate, in an example embodiment. The substrate may be permanently secured to the generally smooth surface 125 of the retractor or may be secured and/or fixed to the generally smooth surface 125 of the retractor to provide a disposable or separately cleanable surface texture for the retractor.

For example, in an example embodiment, a computing entity configured to control a 3D printer is programmed by a user (e.g., via an application operating on the computing entity and/or via opening and/or reading in a file) to print a defined array of partial ellipsoid surfaces 127. The computing entity may then control the 3D printer to cause the 3D printer to print the defined array of partial ellipsoid surfaces 127 directly onto the generally smooth surface 125 of the blade 120 and/or onto a substrate (which may itself by formed by the 3D printer) that may be secured and/or fixed to the blade 120.

In various embodiments, the computing entity comprises at least one processor, at least one non-transitory computer-readable memory storing computer executable instructions (e.g., computer executable instructions for controlling and/or operating the 3D printer), a communications interface (e.g., for communicating via at least one computer and/or communications network, for communicating with the 3D printer, and/or the like), and a user interface for receiving user input (e.g., via a user input device such as a touch screen, mouse, keyboard, microphone, and/or the like) and providing output to a user (e.g., via an output device such as a display, speaker, and/or the like). For example, the computing entity may be configured to receive user input (e.g., via a user input device) defining the array of partial ellipsoid surfaces 127 and user input indicating the 3D printer should be operated and/or controlled to print the defined array of partial ellipsoid surfaces 127. Responsive to receiving and registering (e.g., via the at least one processor) the user input indicating the 3D printer should be operated and/or controlled to print the defined array of partial ellipsoid surfaces 127, computer executable instructions stored in the at least one computer readable memory of the computing entity may be accessed and executed (e.g., by the at least one processor) to cause the computing entity to communicate with the 3D printer (e.g., via the communication interface) to cause, control, and/or operate the 3D printer to print the defined array of partial ellipsoid surfaces 127.

In various embodiments, the array of partial ellipsoid surfaces may take various forms. FIGS. 2A, 2B, 2C, 2D, 2E, 2F, and 2G illustrate some example partial ellipsoid arrays comprising a plurality of partial ellipsoid surfaces 127 disposed on the generally smooth surface 125. In an example embodiment, the plurality of partial ellipsoid surfaces 127 are integrally formed with the generally smooth surface 125. For example, the retractor 100 as a whole may be integrally formed. In an example embodiment, a blade 120 may be integrally formed comprising the generally smooth surface 125 and the plurality of ellipsoid surfaces 127 and configured to be fixedly or selectively secured to a handle 110. In another example embodiment, the plurality of partial ellipsoid surfaces 127 are adhered to the generally smooth surface 125 individually or in groups. In an example embodiment, a sheet or plate having a plurality of partial ellipsoid surfaces 127 thereon may be adhered to the generally smooth surface to adhere a partial ellipsoid array in a single action. In an example embodiment, a sheet or plate having a plurality of partial ellipsoid surfaces 127 and the generally smooth surface 125 may be adhered to the blade 120 to adhere a partial ellipsoid array to the blade 120 in a single action.

Figure 2A:
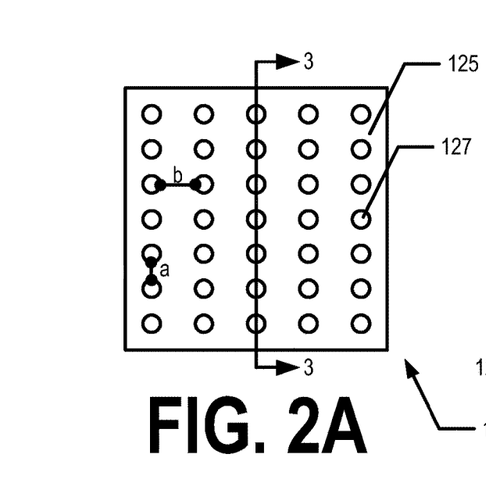
FIGS. 2A, 2B, 2C, 2D, 2E, 2F, and 2G each provide a schematic diagram of an example surface texture in accordance with an example embodiment.
Figure 2B:
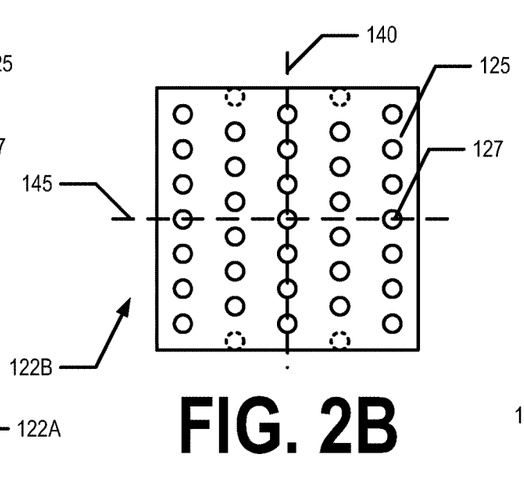

For example, the partial ellipsoid array shown in FIG. 2A comprises a plurality of columns of partial ellipsoid surfaces 127 that are parallel to a first axis 140 of the blade 120. The example partial ellipsoid array shown in FIG. 2A comprises a plurality of rows of partial ellipsoid surfaces 127 that are parallel to a second axis 145 (see FIG. 2B) of the blade 120. The first axis 140 and the second axis 145 are perpendicular to each other. For example, in example embodiments, the plurality of partial ellipsoid surfaces 127 that form the partial ellipsoid array may form and/or define lines that are parallel to the first axis 140 and/or the second axis 145. In the embodiment shown in FIG. 2A, each pair of partial ellipsoid surfaces 127 that are adjacent along the first axis 140 are separated by a first separation distance a and each pair of partial ellipsoid surfaces 127 that are adjacent along the second axis 145 are separated by a second separation distance b. In various embodiments, the first and second separation distances may be equal or different. In various embodiments, the first and second separation distances may be in the range of 0.5 millimeters to 4 millimeters. As shown in FIG. 2B, the plurality of partial ellipsoid surfaces 127 may form a partial ellipsoid array that defines lines that are at an angle with respect to first axis or second axis. For example, the plurality of partial ellipsoid surfaces 127 may form a partial ellipsoid array that defines lines that are 45 degrees with respect to the first and/or second axis 140, 145. In another example, the plurality of partial ellipsoid surfaces 127 may form a partial ellipsoid array that defines lines that define an angle of approximately 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, and/or 85 degrees with respect to one of the first axis 140 and the second axis 145. The dotted circles in FIG. 2B (and FIG. 2F) illustrate optional partial ellipsoid surfaces 127, according to the illustrated example embodiments.

Figure 2C:
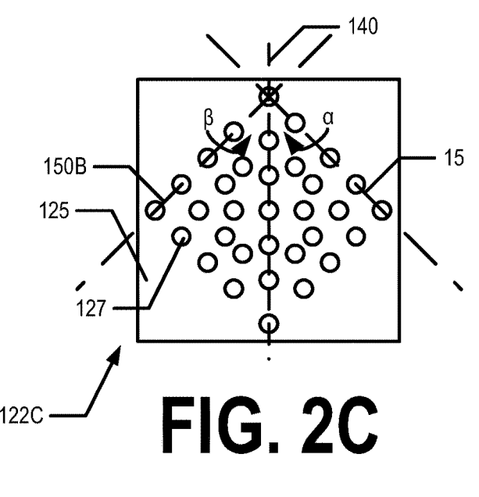

As shown in FIG. 2C, in an example embodiment, the plurality of partial ellipsoid surfaces 127 may form a partial ellipsoid array that is diamond and/or quadrilateral in nature. For example, the plurality of partial ellipsoid surfaces 27 may form a partial ellipsoid array in which a first portion of the partial ellipsoid array comprises lines that are at a first angle to the first axis 140 and a second portion of the partial ellipsoid array comprises lines that are at a second angle to the first axis 140, wherein the first angle is not equal to the second angle. For example, in FIG. 2C, a first portion of the partial ellipsoid array comprises lines parallel to line 150A that are at a first angle α with respect to the first axis 140 and a second portion of the partial ellipsoid array comprises lines parallel to line 150B that are at a second angle β with respect to the first axis, wherein α and β are not equivalent. For example, in the illustrated example, α is approximately −β.

Figure 2D:
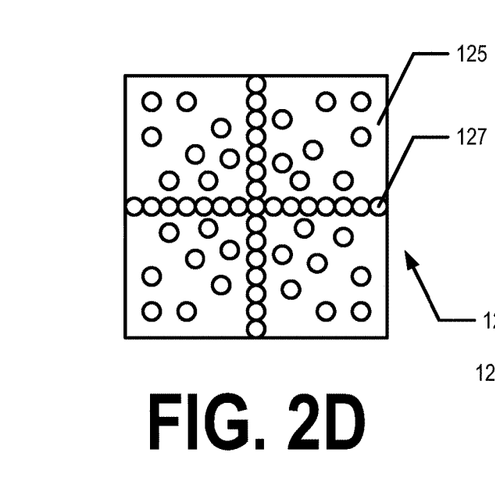

FIG. 2D illustrates an example partial ellipsoid array in which some of the plurality of partial ellipsoid surfaces 127 abut at least one other partial ellipsoid surface, while other partial ellipsoid surfaces 127 are spaced apart from the adjacent partial ellipsoid surfaces. For example, FIG. 3A shows a cross-section of the partial ellipsoid array illustrated in FIG. 2A. Each of the partial ellipsoid surfaces 127 are spaced from the adjacent partial ellipsoid surfaces 127 by a spacing distance of s. In the case of the embodiment shown in FIG. 2A, the spacing s is the first separation distance a. The spacing s between a first partial ellipsoid surface 127 and a second partial ellipsoid surface 127 is the shortest distance between the one dimensional curve (e.g., line) where the first partial ellipsoid surface 127 touches, meets, intersects, and/or the like the generally smooth surface 125 and the one dimensional curve (e.g., line) where the second partial ellipsoid surface 127 touches, meets, intersects, and/or the like the generally smooth surface 125, wherein the first and second partial ellipsoid surfaces 127 are adjacent and/or directly neighboring partial ellipsoid surfaces. In an example embodiment, at least some of the partial ellipsoid surfaces 127 of the partial ellipsoid array abuts at least one adjacent and/or directly neighboring partial ellipsoid surface, as shown in FIG. 2D. For example, in an example embodiment, the smallest spacing of the partial ellipsoid array is s=0 for at least one partial ellipsoid surface 127 (and its adjacent and/or directly neighboring partial ellipsoid surface). In another example embodiment, the smallest spacing of the partial ellipsoid array is in the range 0.5 millimeters to 1 centimeter (e.g., in the embodiments illustrated in FIGS. 2A, 2B, 2C, 2E, and 2F). For example, in one embodiment, the spacing between a partial ellipsoid surface 127 and the directly adjacent and/or neighboring partial ellipsoid surfaces is in the range of 1 millimeter to 1 centimeter. In an example embodiment, the spacing between a first partial ellipsoid surface and an adjacent second partial ellipsoid surface is approximately 0.75 millimeters to 1.75 millimeters. For example, in one embodiment, the spacing between a partial ellipsoid surface 127 and the directly adjacent and/or neighboring partial ellipsoid surfaces is 2 millimeters. In an example embodiment, the spacing s between adjacent and/or directly neighboring partial ellipsoid surfaces 127 is consistent throughout the partial ellipsoid array. In another embodiment, the partial ellipsoid array may define two or more spacings s. For example, in one embodiment, a spacing between the first partial ellipsoid surface and the second partial ellipsoid surface is approximately 0.5 millimeters to 1 centimeter while at least some of the plurality of partial ellipsoid surfaces are separated from a directly adjacent one of the plurality of partial ellipsoid surfaces by a separation within the range of 1 millimeter to 1 centimeter.

Figure 2E:
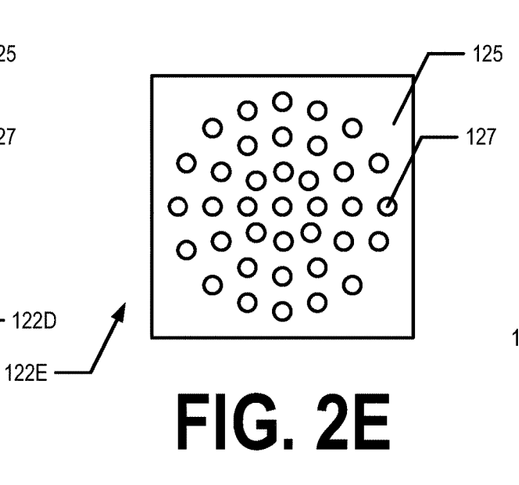
Figure 2F:
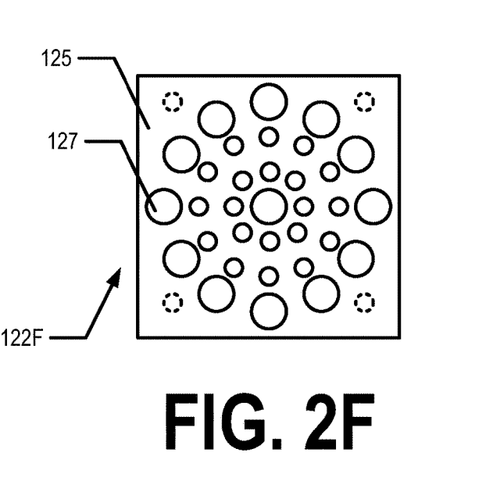
Figure 3A:
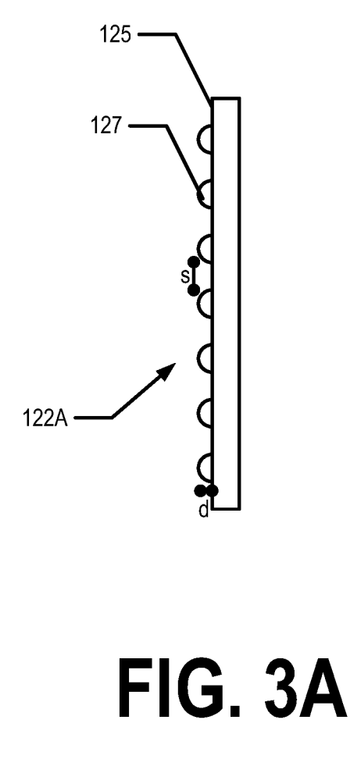
FIGS. 3A, 3B, and 3C provide cross-sections of example embodiments of the surface texture shown in FIG. 2A.

FIG. 2E illustrates an example embodiment in which the partial ellipsoid array is organized into a series of concentric circles. The partial ellipsoid array of FIG. 2E comprises a plurality of partial ellipsoid surfaces 127 that are the same size (e.g., have the same major, intermediate, minor axis lengths). FIG. 2F illustrates an example embodiment wherein the partial ellipsoid array is primarily organized into a series of concentric circles and the plurality of partial ellipsoid surfaces 127 comprises a plurality of partial ellipsoid surfaces 127 that are of a first size and a plurality of partial ellipsoid surfaces 127 that are of a second size, wherein the first size and the second size are not equivalent. In various embodiments, the partial ellipsoid array may take various forms, as appropriate for the application.

Figure 2G:
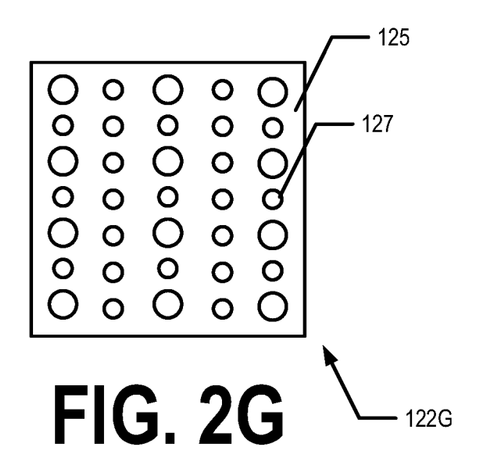

For example, the partial ellipsoid array shown in FIG. 2G comprises a plurality of columns of partial ellipsoid surfaces 127 that are parallel to a first axis 140 of the blade 120 to provide a tissue contact surface 122G. In the embodiment shown in FIG. 2G, a first column of partial ellipsoid surfaces 127 may comprise alternating partial ellipsoid surfaces of a first size and partial ellipsoid surfaces of a second size. For example, in a first column, the partial ellipsoid surfaces of a first size may be adjacent partial ellipsoid surfaces of a second size. A second column adjacent the first column may comprise only partial ellipsoid surfaces 127 of the first size. A third column adjacent the second column may comprise alternating partial ellipsoid surfaces of the first size and the second size in the same manner as the first column.

Figure 3B:
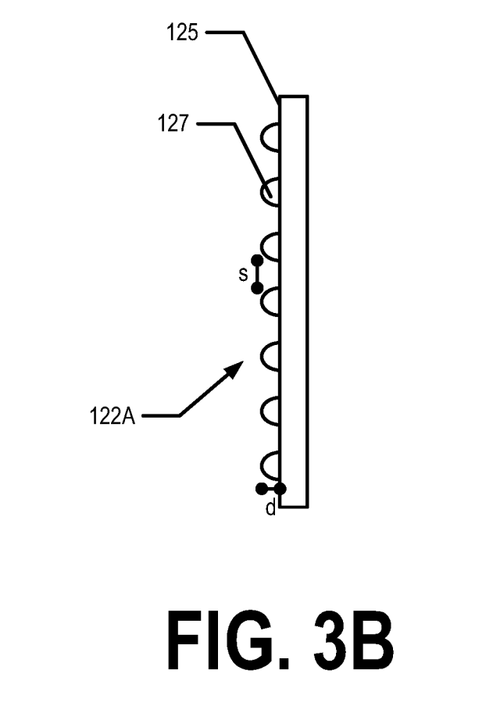
Figure 3C:
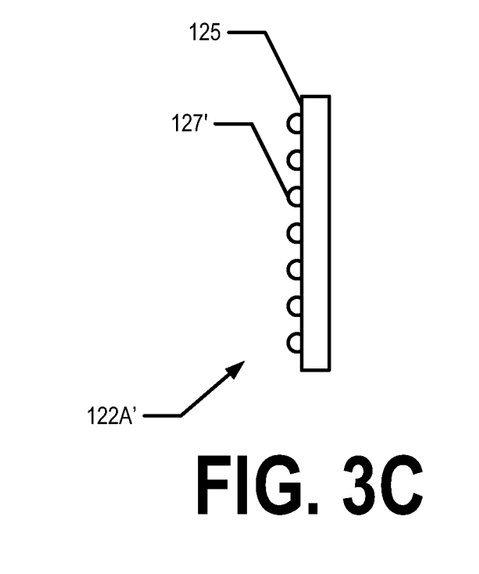

FIGS. 3A, 3B, and 3C show cross-sections of three different embodiments of tissue contact surfaces 122A that have similar partial ellipsoid arrays. In the embodiment shown in FIG. 3A, the volume defined by a partial ellipsoid surface is up to 50% of the volume defined by a complete ellipsoid surface defined by the same major, intermediate, and minor axes as the partial ellipsoid surface 127. For example, in an example embodiment in which the partial ellipsoid surfaces 127 are partial spherical surfaces, the partial spherical surfaces may be hemispheres and define a volume that is 50% of the volume defined by a complete sphere defined by the same radius as the partial ellipsoid surface 127. For example, the partial ellipsoid surfaces 127 may extend a distance d from the generally smooth surface 125. In an example embodiment, the distance d is the major, minor, or intermediate axis length for the partial ellipsoid surface 127. In the embodiment shown in FIG. 3C, the volume defined by a partial ellipsoid surface is greater than 50% (but no more than 100%) of the volume defined by a complete ellipsoid surface defined by the same major, intermediate, and minor axes as the partial ellipsoid surface 127. In various embodiments, the percentage of the volume of a corresponding complete ellipsoid surface defined by a partial ellipsoid surface 127 may be determined based on the application. FIG. 3B illustrates another example cross-section of tissue contact surface 122A, wherein the partial ellipsoid surfaces 127 extend a length d from the generally smooth surface 125 and the length d is the major axis length of the partial ellipsoid surfaces 127.

In an example embodiment, the plurality of partial ellipsoid surfaces 127 cover a portion of the area of the generally smooth surface 125. In various embodiments, the plurality of partial ellipsoid surfaces 127 cover up to 25% of the area of the generally smooth surface 125. In another example embodiment, the plurality of partial ellipsoid surfaces 127 cover 25% to 50% of the area of the generally smooth surface 125. In an example embodiment, the plurality of partial ellipsoid surfaces 127 cover up to 75%, up to 80%, up to 90% or up to 95% of the area of the generally smooth surface 125.

In various embodiments, the surgical retractor 100 may formed, molded, carved, machined, and/or the like as single element comprising the handle 110, blade 120, generally smooth surface 125, and the plurality of partial ellipsoid surfaces 127. In an example embodiment, a blade may be formed, molded, carved, machined, and/or the like comprising the generally smooth surface 125 and the plurality of partial ellipsoid surfaces 127 that may be fixedly secured to an appropriate handle 110. In an example embodiment, a surgical retractor 100 having a handle 110 and a blade 120 may be retrofitted with a generally smooth surface 125 and a plurality of partial ellipsoid surfaces 127. For example, a plate or sheet comprising the generally smooth surface 125 and the plurality of partial ellipsoid surfaces 127 may be fixedly or selectively secured to the blade 120. For example, such a plate or sheet could be adhered to, welded to, bonded to, coupled to, and/or the like to fixedly and/or selectively secure the plate or sheet comprising the generally smooth surface 125 and the partial ellipsoid array to the blade 120. For example, the plate or sheet may be configured to be selectively secured to the blade 120 such that the plate or sheet comprising the generally smooth surface 125 and the plurality of ellipsoid surfaces 127 may be removed for cleaning and/or such that a particular ellipsoid array may be selected for us in a particular surgical procedure.

While this disclosure refers to partial ellipsoid surfaces 127, in an alternate embodiment, the partial ellipsoid surfaces are a truncated cone or a truncated pyramid with smoothed edges. In particular, the partial ellipsoid surfaces 127 (and any alternative embodiments) need only not comprise any sharp edges, so as to not damage tissue engaged by the retractor 100, and thus be generally easy to clean.

Tests were conducted to determine the translational force of a control first surface and various example embodiment surfaces. The translational force generally describes how the surface interacts with other surfaces. In particular, the translational force tests determines the amount of force required to translate or drag a first surface along a second surface. For example, the higher the translational force corresponding to a first surface, the less likely the first surface will slip against a second surface (e.g., tissue) when pressure is applied press the first surface against the second surface. According to the conducted tests, the control surface (a tissue contact surface with no partial ellipsoid surfaces 127) has a translational force (divided by the acceleration of gravity g) of approximately 150 g.

Figure 4A:
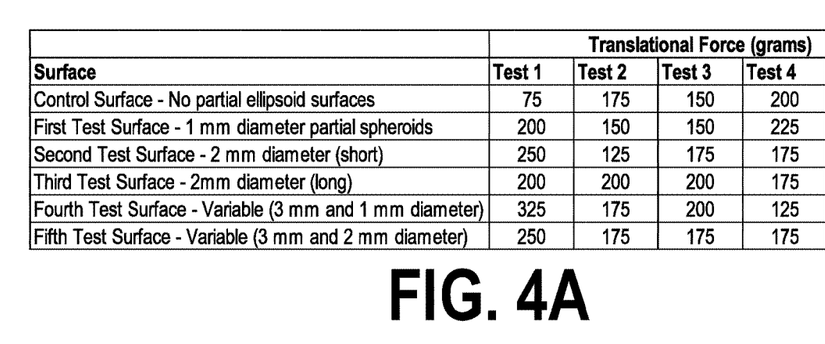
FIGS. 4A and 4B provide a table and a data plot summarizing the results of test results of five example test surfaces in accordance with various embodiments of the present invention compared to a control surface.
Figure 4B:
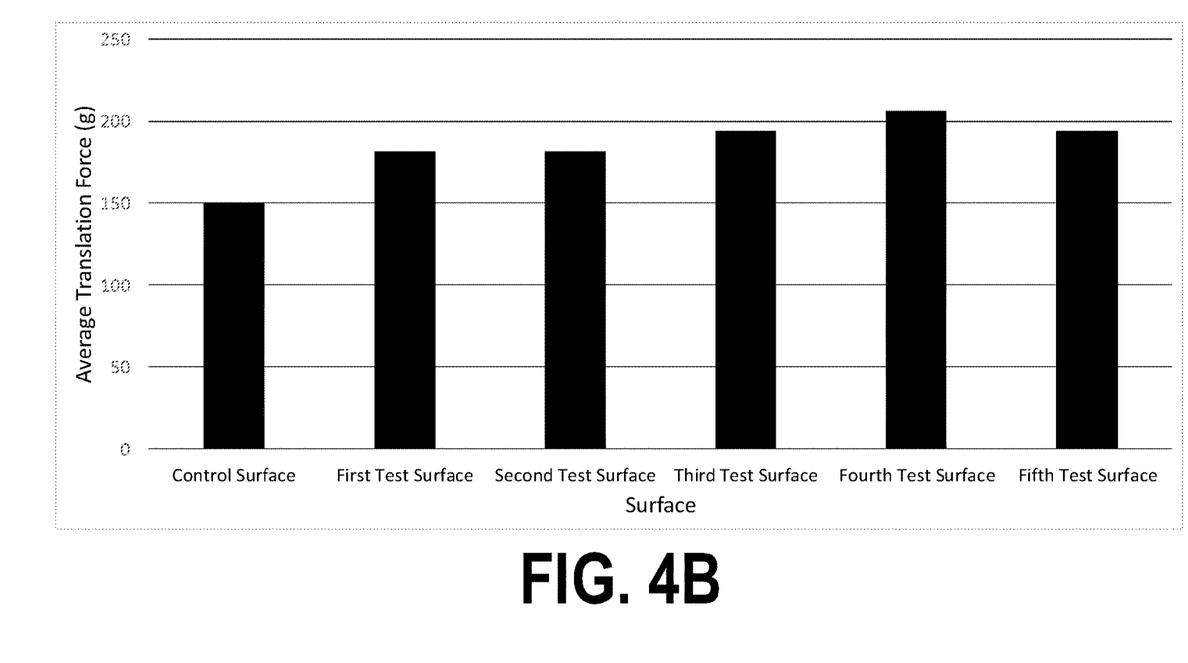

Five different example embodiment tissue contact surfaces 122 were tested, which are referred to as test surfaces herein. FIG. 4A provides a table summarizing the results of the testing the five example embodiment tissue contact surfaces 122 and FIG. 4B provides a data plot providing a graphical representation of the testing results. The first test surface is similar to the example tissue contact surface 122A shown in FIG. 2A with both the first separation distance a and the second separation distance b being 1 millimeter and each of the partial ellipsoid surfaces 127 defining a circle on the generally smooth surface 125 having a 1 millimeter diameter. The cross-section of the first test surface is similar to that shown in FIG. 3A with the length d being 1 millimeter. The second test surface is similar to the example tissue contact surface 122 shown in FIG. 2A with both the first separation distance a and the second separation distance b being 2 millimeters and the partial ellipsoid surfaces 127 defining a circle on the generally smooth surface 125 having a 2 millimeter diameter. The second test surface has a cross-section similar to that shown in FIG. 3A with the length d being 2 millimeters. The third test surface is similar to the example tissue contact surface 122 shown in FIG. 2A with both the first separation distance a and the second separation distance b being 2 millimeter and the partial ellipsoid surfaces 127 defining a circle on the generally smooth surface 125 having a 2 millimeter diameter. The cross-section of the third test surface is similar to that shown in FIG. 3B with the length d being 3 millimeters. The fourth test surface is similar to the tissue contact surface 122G shown in FIG. 2G wherein partial ellipsoid surfaces 127 comprise partial ellipsoid surfaces 127 of a first size and partial ellipsoid surfaces of a second size. The first size partial ellipsoid surfaces define a circle on the generally smooth surface 125 having a 1 millimeter diameter and the second size partial ellipsoid surfaces define a circle on the generally smooth surface 125 having a 3 millimeter diameter. The cross-section of the fourth test surface is similar to that shown in FIG. 3A, however, the length d for the partial ellipsoid surfaces of the first size is 1 millimeter and the length d for the partial ellipsoid surfaces of the second size is 3 millimeters. The fifth test surface is also similar to the tissue contact surface 122G shown in FIG. 2G wherein partial ellipsoid surfaces 127 comprise partial ellipsoid surfaces 127 of a first size and partial ellipsoid surfaces of a second size. The first size partial ellipsoid surfaces define a circle on the generally smooth surface 125 having a 2 millimeter diameter and the second size partial ellipsoid surfaces define a circle on the generally smooth surface 125 having a 3 millimeter diameter. The cross-section of the fourth test surface is similar to that shown in FIG. 3A, however, the length d for the partial ellipsoid surfaces of the first size is 2 millimeter and the length d for the partial ellipsoid surfaces of the second size is 3 millimeters.

In various embodiments, the tissue contact surface 122 has a translational force in the range of 175 to 250 g. Thus, various embodiments provide a tissue contact surface 122 that has a translational force that is 25-40% greater than the measured translational force of the control surface. For example, the average measured translational force for the first test surface was 181.25 grams. The average measured translational force for the second test surface was 181.25 grams. The average measured translational force for the third test surface was 193.75 grams. The average measured translational force for the fourth test surface was 206.25 grams. The average measured translational force for the fifth test surface was 193.75 grams. Thus, various embodiments of the tissue contact surface 122 comprising the partial ellipsoid array have greater translational forces than the control surface. Thus, the retractor 100 comprising the tissue contact surface 122 comprising a generally smooth surface 125 and a partial ellipsoid array thereon provides an improvement over a generally smooth retractor while still reducing and/or minimizing the damage to the contacted tissue.

In various embodiments, a second consideration is used to determine the layout of the partial ellipsoid array. For example, in various embodiments, a first consideration of the translational force or coefficient of friction may be used to select a partial ellipsoid array for a tissue contact surface 122. In various embodiments, the first consideration of the translation force or coefficient of friction and a second consideration (e.g., the ease of cleaning the tissue contact surface 122) may be used to select a partial ellipsoid array for a tissue contact surface 122. For example, after each use of the retractor 100 and/or tissue contact surface 122, the tissue contact surface 122 must be thoroughly cleaned. Therefore, in an example embodiment, it is advantageous to have a retractor 100 having a tissue friendly tissue contact surface 122 with an increased coefficient of friction and/or translation force (with respect to the control surface) but that is also easy to thoroughly clean. For example, in such an instance, the first test surface may be selected as an optimal tissue contact surface 122.

According to an example embodiment, the ideal surface pattern would be partial ellipsoid surfaces that are partial spheroid surfaces defined by a 1 millimeter diameter spheres that are arranged in rows with first and second separation distances of 1 millimeter, such as the first test surface. In the performed tests, the first test surface gave a 25% increase in force required to slide against the tissue surface and was easy to clean. Thus, the first test surface would allow a retractor 100 to be placed into position with the least amount of difficulty, improve the ability of the retractor to engage the tissue without damaging the tissue, and be easy to clean. For example, an ideal surface pattern may comprise a plurality of partial ellipsoid surfaces extending out and away from the generally smooth surface, where a first partial ellipsoid surface of the plurality of partial ellipsoid surfaces extends approximately 0.75-1.25 millimeters out from the generally smooth surface, and a spacing between the first partial ellipsoid surface and a second partial ellipsoid surface of the plurality of partial ellipsoid surfaces is approximately 0.75-1.25 millimeters. In an example embodiment, the plurality of partial ellipsoid surfaces comprise spherical surfaces. In an example embodiment, the plurality of partial ellipsoid surfaces defines a periodic array (e.g., columns and/or rows or concentric circles of partial ellipsoid surfaces).

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A surgical retractor comprising:
a blade having a first tissue contact surface, the first tissue contact surface comprising a first generally smooth surface having at least one edge and defining a first axis, the first axis being parallel to the at least one edge; and a first plurality of partial ellipsoid surfaces extending out and away from the first generally smooth surface, wherein (a) each of the first plurality of partial ellipsoid surfaces extends approximately 0.5 millimeters to 1 centimeter out from the first generally smooth surface and (b) each of the first plurality of partial ellipsoid surfaces defines a major axis and a minor axis and one of the major axis or the minor axis is parallel to the first axis of the first generally smooth surface; and
a handle secured to an end of the blade, a portion of the handle comprising a second tissue contact surface comprising a second generally smooth surface and a second plurality of partial ellipsoid surfaces extending outward from the second generally smooth surface, wherein the first generally smooth surface and the second generally smooth surface are transverse to each other,
wherein the first plurality of partial ellipsoid surfaces form columns parallel to the first axis of the first generally smooth surface with a first separation distance of approximately 1 mm,
the first plurality of partial ellipsoid surfaces form rows parallel to a second axis of the first generally smooth surface with a second separation distance of approximately 1 mm, and
the first axis is perpendicular to the second axis.

2. The surgical retractor of claim 1, wherein the first plurality of partial ellipsoid surfaces are 3D printed onto the first generally smooth surface.

3. The surgical retractor of claim 1, wherein the first tissue contact surface is configured and/or operable to (a) retract and/or expose tissue during a surgical procedure and (b) to provide increased friction between the tissue and the first tissue contact surface compared to a surgical retractor having only a planar surface without damaging and/or while minimizing damage to the tissue contacted by the first tissue contact surface.

4. The surgical retractor of claim 1, wherein the major axis and the minor axis are both within the range of 0.5 millimeters and 1 centimeter.

5. The surgical retractor of claim 1, wherein each of the first plurality of partial ellipsoid surfaces extends approximately 0.75 millimeters to 1.25 millimeters out from the first generally smooth surface.

6. The surgical retractor of claim 1, wherein the columns are equally-spaced.

7. The surgical retractor of claim 1, wherein an axis of at least one of the first plurality of partial ellipsoid surfaces is parallel to a normal of the first generally smooth surface at the location of the at least one of the first plurality of partial ellipsoid surfaces.

8. The surgical retractor of claim 1, wherein first plurality of partial ellipsoid surfaces consist of partial spheroid surfaces defined by a diameter of 1 millimeter.

* * * * *

UNITED STATES PATENT AND TRADEMARK OFFICE
CERTIFICATE OF CORRECTION

PATENT NO. : 11,684,353 B2
APPLICATION NO. : 16/644542
DATED : June 27, 2023
INVENTOR(S) : Benjamin K. Wilke et al.

Page 1 of 1

It is certified that error appears in the above-identified patent and that said Letters Patent is hereby corrected as shown below:

In the Claims

Column 12
Line 35, Claim 8 "wherein first" should read --wherein the first--

Signed and Sealed this
Fifteenth Day of August, 2023

Katherine Kelly Vidal
*Director of the United States Patent and Trademark Office*